United States Patent [19]

Jikuya et al.

[11] Patent Number: 5,043,264
[45] Date of Patent: Aug. 27, 1991

[54] DNA PROBES FOR DETECTING SALMONELLA AND A METHOD FOR DETECTING SALMONELLA THEREWITH

[75] Inventors: Hiroyuki Jikuya, Nagaokakyo; Tetuo Ohashi, Tushima; June Takano, Kyoto, all of Japan

[73] Assignee: Shimadzu Corporation, Kyoto, Japan

[21] Appl. No.: 376,005

[22] Filed: Jul. 6, 1989

[30] Foreign Application Priority Data

Jul. 29, 1988 [JP] Japan .................................. 63-191490

[51] Int. Cl.$^5$ .......................... C12Q 1/68; C07H 21/04
[52] U.S. Cl. ............................................ 435/6; 435/91; 435/879; 436/501; 436/811; 536/27; 935/9; 935/19; 935/78
[58] Field of Search ................. 435/6, 91, 879; 436/501, 811; 536/27; 935/9, 19, 78

[56] References Cited

U.S. PATENT DOCUMENTS 4,358,535 11/1982 Falkow et al. ........................ 435/5

OTHER PUBLICATIONS

Clarke et al. (1982), Gene, vol. 18, pp. 157-163.

*Primary Examiner*—Robert A. Wax
*Assistant Examiner*—Ardin H. Marschel
*Attorney, Agent, or Firm*—Birch, Stewart, Kolasch & Birch

[57] ABSTRACT

A novel probe for detecting Salmonella comprises:
a labeled substance, and
a DNA or RNA fragment which hybridizes with a base sequence having the following formula (I), or (II) being complementary to the formula (I).

5'-GCTCAGACGTATGGCGGTA-3'     (I)

3'-CGAGTCTGCATACCGCCAT-5'     (II)

This invention also provides a method for detecting Salmonella by using the probe.

The probe reduces the time required for detecting Salmonella.

17 Claims, No Drawings

DNA PROBES FOR DETECTING SALMONELLA AND A METHOD FOR DETECTING SALMONELLA THEREWITH

FIELD OF THE INVENTION

This invention relates to a DNA probe which detects Salmonella in a sample from human beings, other animals, foods, or other products, and a method for detecting Salmonella.

BACKGROUND OF THE INVENTION

Diseases caused by infection of Salmonella (Salmonella infectious disease) are classified into a typhoidal type disease and an acute gastroenteritis type disease. In either type of disease, a significant test item to identify the diseases is detection of Salmonella in a sample such as blood, feces, and urine. The detection of Salmonella is a significant test item also to confirm the safety of foods or the like.

The most general method for detecting Salmonella is as follows:

A sample is firstly inoculated on a Hajna Tetrathionate broth culture medium or the like, and cultivation is carried out for 18-24 hours to proliferate bacteria before isolation cultivation on a DHL agar medium for 24 hours. Then, originated black colonies are cultured on a TSI agar and a LIM medium for 18-24 hours, and thereafter the primary identification test is carried out before a serological examination or the like to detect the existence of Salmonella.

A conventional detection method for Salmonella, mainly consisting of such a cultivation, has the following problems:

Firstly, an examination can not be performed after treatment with antibiotics or the like. Secondly, there is required a long time of more than several days before obtaining an examination result.

OBJECTS AND SUMMARY OF THE INVENTION

It is an object of the present invention to reduce the time required for an examination by remarkably reducing the cultivation period. The reduction of examination time is important to perform a suitable treatment for a patient of Salmonella infectious disease, and to prevent Salmonella from spreading.

The present invention is based on the investigation that a base sequence having a formula (I) below is specific to bacteria of Salmonella genus, in which the base sequence is contained in the extensive base sequence of an ara C gene of *Salmonella typhimurium* reported in Gene 18, 157-163(1982) by P. Clarke et. al. The invention provides a method for detecting Salmonella in a sample by detecting a DNA having the base sequence of a formula (I) or a complementary formula (II) thereto.

A novel probe for detecting Salmonella of the present invention comprises:
a labeled substance, and
a DNA or RNA fragment which hybridizes with a base sequence having the following formula (I), or (II) being complementary to the formula (I).

5'-GCTCAGACGTATGGCGGTA-3'  (I)

3'-CGAGTCTGCATACCGCCAT-5'  (II)

The present invention also provides a method for detecting Salmonella in a sample, which comprises:
contacting said probe with a sample under the condition in which the probe can hybridize with a Salmonella DNA, and
detecting the existence of a DNA-DNA or DNA-RNA complex.

DETAILED DESCRIPTION OF THE INVENTION

The probe for detection comprises a moiety which recognizes the base sequence of a formula (I) or (II) to hybridize with it, and a labeled substance combined with the moiety.

That is, the DNA probe comprises a labeled substance and a DNA fragment which has a base sequence having the following formula (I) or (II).

5'-GCTCAGACGTATGGCGGTA-3'  (I)

3'-CGAGTCTGCATACCGCCAT-5'  (II)

On the other hand, the RNA probe comprises a labeled substance and a RNA fragment which has a base sequence having the following formula (I') or (II').

5'-GCUCAGACGUAUGGCGGUA-3'  (I')

3'-CGAGUCUGCAUACCGCCAU-5'  (II')

Although there may be used DNA or RNA which has the complementary base sequence to that of a formula (I) or (II) as the moiety for hybridization, DNA is preferably used due to stability as a reagent. Although the length of the probe DNA is not necessarily limited to that of base sequence complementary to the nineteen bases of formulae (I) and (II), unnecessary long probe DNAs are not preferable because they are liable to have increased binding affinity to bacteria DNAs other than Salmonella.

The probe DNA may be prepared by cleaving Salmonella DNAs with a restriction enzyme or the like, and by a chemical synthesis method such as a diester, triester, phosphite, phosphoramide method, or the like. The probe RNA is also prepared by the above conventional methods.

The labeled substance to be combined with the probe DNA or RNA, may be a radioisotope, a fluorescent agent, enzyme, luminescent agent, etc. These substances may be directly combined or indirectly combined through avidin or antibody with the probe DNA or RNA.

The probe of the present invention can be used in a colony hybridization method, or other detection methods in which hybridization is carried out. For detecting Salmonella, DNA obtained by lysis of subject bacteria is immobilized on a membrane of nitrocellulose or nylon, and then an excess of the probe of the present invention is added to the DNA to form a hybrid.

The bacteria may be broken by an alkali solution, surfactant, lytic enzyme or the like. The DNA from the bacteria can be immobilized on the membrane by baking at about 80° C. or by exposing the membrane to ultraviolet light. A hybridized probe is immobilized, and a probe not hybridized is removed by washing.

After washing, the labeled substance of the hybridized probe is detected. The detection method differs with each kind of labeled substances. The probe labeled by a radioisotope can be detected by a scintillation counter or other radiation measuring instruments, or an autoradiography method using exposure of a film. The amount of the hybridized DNA can be measured by a fluorescent measuring instrument when the probe contains a fluorescent substance, or by measuring enzyme activity when the probe is labeled with an enzyme.

EXAMPLE

Preparation of the DNA Probe

A sequence of 5'-GCTCAGACGTATGGCGGTA-3' was selected from the base sequence of an ara C gene in *Salmonella typhimurium* (P. Clarke et. al., Gene 18, 157–163(1982)). Then, oligonucleotide (probe I) having the same sequence as said gene and oligonucleotide (probe II) having a complementary sequence to said gene were prepared by chemical synthesis. That is, probe I and probe II have the base sequences of the following formulae:

5'-GCTCAGACGTATGGCGGTA-3'    Probe I

3'-CGAGTCTGCATACCGCCAT-5'    Probe II

Chemical synthesis was carried out by a triester method with a DNA synthesis instrument (Model NS-1 by Shimadzu Corporation). The synthesized DNA fragments were purified with a $C_{18}$ reverse-phase column. Each of the resulting DNA fragments was labeled with $[\gamma-^{32}P]$ ATP by polynucleotide kinase.

Colony Hybridization

Colony hybridization was carried out by using 4 strains of bacteria in Salmonella genus and 17 strains of bacteria in other genus to examine specificity of the DNA probes as follows.

Each nitrocellulose membrane sterilized by an autoclave was put onto an agar plate culture medium, and the test strains were grown on the membrane. According to the method of Mosley et. al. (J. Infect. Dis., 892–898(1980)), the bacteria were lysed with 0.5M solution of sodium hydroxide, and were neutralized and dried. Thereafter, the bacterial DNAs were immobilized on the nitrocellulose membrane at 80° C. Each membrane was reacted at 35° C. for one hour in a hybridization solution (6×SSC, 5 ×Denhardt's solution, 1 mM EDTA, 100 μg/ml of a salmon sperm DNA) including $10^6$ cpm of the DNA probe per 1 cm² of the membrane, and then washed with 1×SSC (50° C. or 55° C.) for five minutes×three times. The membrane was dried, and then the formation of hybridization was examined with an autoradiography. The results are shown in Table 1.

As shown in Table 1, it is found that a probe I and a probe II, having a complementary base sequence to a probe I, is hybridized only with the bacteria in *Salmonella* genus, and is not reacted with other bacteria, at a washing temperature of 55° C.

TABLE 1

Effect of temperature of a washing solution onto hybridization of a DNA probe and bacteria DNA

| Name of test strain | Number of strain | Probe I 50° C. | Probe I 55° C. | Probe II 50° C. | Probe II 55° C. |
|---|---|---|---|---|---|
| Salmonella enteritidis | 1 | + | + | + | + |
| Salmonella typhi | 2 | + | + | + | + |
| Salmonella typhimurium | 1 | + | + | + | + |

TABLE 1-continued

Effect of temperature of a washing solution onto hybridization of a DNA probe and bacteria DNA

| Name of test strain | Number of strain | Probe I 50° C. | Probe I 55° C. | Probe II 50° C. | Probe II 55° C. |
|---|---|---|---|---|---|
| Escherichia coli | 2 | ± | − | ± | − |
| Klebsiella pneumoniae | 1 | ± | − | ± | − |
| Proteus vulgaris | 1 | − | − | − | − |
| Pseudomonas aeruginasa | 1 | ± | − | ± | − |
| Shigella dysenteriae | 2 | ± | − | ± | − |
| Shigella flexneri | 1 | ± | − | ± | − |
| Shigella sonnei | 2 | + | − | + | − |
| Vibrio cholerae | 4 | ± | − | ± | − |
| Vibrio parahaemolyticus | 2 | ± | − | ± | − |
| Yersinia enterocolitica | 1 | ± | − | ± | − |

EFFECTS OF THE INVENTION

The DNA and RNA probes of the present invention have a characteristic in that the probes react specifically with the *Salmonella* DNA, whereby the probes can easily detect *Salmonella* from a sample containing various kinds of bacteria. Therefore, the probes can identify *Salmonella* without needful cultivation for bacteria isolation in a conventional detection method, and shortens an examination period. The probes have an advantage that the causative bacteria of disease can be identified even after death of bacteria by antibiotics.

Further, the DNA probes of the present invention are characterized by consisting of 19 nucleotides having the identified sequence, and hence, the DNA probes have the following advantages in comparison with a current probe consisting of thousands of nucleotides: Firstly, the probes having a stable quality can be prepared since they can be easily prepared by chemical synthesis, and the cost of preparation thereof can be decreased since they are suitable for mass production. Secondly, a reaction time can be reduced since the probes can be processed in a higher concentration. Thirdly, since a whole sequence of each probe is identified, the probe has an advantage that functional alteration, such as alteration of the optimum washing temperature without alteration of specificity to bacteria, can be easily carried out by addition of other nucleotides or a certain modification in the base sequence.

What is claimed is:

1. A DNA or RNA probe for detecting Salmonella consisting of:

a labeled DNA or a labeled RNA fragment consisting of a base sequence having a formula selected from the group consisting of:

5'-GCTCAGACGTATGGCGGTA-3'    (I);

3'-CGAGTCTGCATACCGCCAT-5'    (II);

5'-GCUCAGACGUAUGGCGGUA-3'    (I'); and

3'-CGAGUCUGCAUACCGCCAU-5'    (II').

2. The probe of claim 1, which is a DNA probe consisting of the base sequence 5'-GCTCAGACGTATGGCGGTA-3' (I).

3. The probe of claim 1, which is a DNA probe consisting of the base sequence 3'-CGAGTCT-GCATACCGCCAT-5' (II).

4. The probe of claim 1, which is a RNA probe consisting of the base sequence 5'-GCUCAGAC-GUAUGGCGGUA-3' (I').

5. The probe of claim 1, which is a RNA probe consisting of the base sequence 3'-CGAGUCUG-CAUACCGCCAU-5' (II').

6. The DNA probe of claim 1, which is a DNA probe labeled with a radioisotope, a fluorescent agent, an enzyme or a luminescent agent.

7. The RNA probe of claim 1, which is an RNA probe labeled with a radioisotope, a fluorescent agent, an enzyme or a luminescent agent.

8. The probe of claim 2, which is labeled with $^{32}P$.

9. The probe of claim 3, which is labeled with $^{32}P$.

10. The probe of claim 4, which is labeled with $^{32}P$.

11. The probe of claim 5, which is labeled with $^{32}P$.

12. A method for testing for the presence of Salmonella in a sample, which comprises:
   contacting the probe of claim 1 with a sample under conditions in which the probe can selectively hybridize with a Salmonella DNA, if present, but not hybridize with DNA from other bacteria; and
   detecting the existence of a DNA-probe hybridization complex.

13. The method of claim 12, which comprises the step of removing probe which has not hybridized with the sample prior to the detecting step.

14. The method of claim 12, which comprises the steps of:
   lysing bacteria in the sample to be tested to release DNA contained in said bacteria;
   immobilizing said released DNA on a substrate;
   contacting said immobilized DNA with said probe under conditions which allow to hybridize with Salmonella DNA, if present, but not hybridize with DNA from other bacteria;
   removing probe which has not hybridized with said immobilized DNA; and
   detecting the existence of a DNA-probe hybridization complex.

15. A method for testing for the presence of Salmonella in a sample, which comprises:
   contacting the probe of claim 1 with a sample under conditions in which the probe can strongly hybridize with Salmonella DNA, if present, but the probe does not strongly hybridize with DNA from other bacteria;
   separating probe which has not strongly hybridized with said DNA; and
   detecting the presence of a DNA-probe hybridization complex.

16. The method of claim 15, which comprises the steps of:
   immobilizing said sample on a nitrocellulose membrane;
   contacting said immobilized DNA with a hybridization solution containing said probe at 35° C. for one hour;
   washing said nitrocellulose membrane to remove probe which has not strongly hybridized with said DNA; and
   detecting the presence of a DNA-probe hybridization complex by autoradiography, said probe being a radioactively labeled probe.

17. The method of claim 16, wherein said hybridization solution contains 6×SSC, 5×Denhardt's solution, 1 mM EDTA and 100 μg/ml salmon sperm DNA.

* * * * *